United States Patent [19]

Kummer et al.

[11] 4,350,572

[45] Sep. 21, 1982

[54] PURIFICATION OF CARBOXYLIC ACID ESTERS CONTAINING ALDEHYDES AND/OR ACETALS

[75] Inventors: Rudolf Kummer, Frankenthal; Volker Taglieber, Ludwigshafen; Franz-Josef Weis, Weinheim; Heinz-Walter Schneider, Ludwigshafen, all of Fed. Rep. of Germany

[73] Assignee: BASF Aktiengesellschaft, Fed. Rep. of Germany

[21] Appl. No.: 204,637

[22] Filed: Nov. 6, 1980

[30] Foreign Application Priority Data

Dec. 6, 1979 [DE] Fed. Rep. of Germany ....... 2949073

[51] Int. Cl.$^3$ .............................................. B01D 3/34
[52] U.S. Cl. ...................................... 203/35; 560/248
[58] Field of Search ................................... 203/34, 35; 560/231–233, 241, 243–245, 247, 248

[56] References Cited

U.S. PATENT DOCUMENTS 2,741,632 4/1956 Cottle ..................................... 203/34
3,573,689 5/1971 Martin et al. ......................... 560/248

*Primary Examiner*—Frank Sever
*Attorney, Agent, or Firm*—Keil & Witherspoon

[57] ABSTRACT

A process for purifying carboxylic acid esters which have been obtained by reacting olefinically unsaturated compounds with carbon monoxide and alkanols and which contain aldehydes or acetals, wherein the said esters are treated with a strongly acidic agent, with or without addition of water.

7 Claims, No Drawings

PURIFICATION OF CARBOXYLIC ACID ESTERS CONTAINING ALDEHYDES AND/OR ACETALS

Carboxylic acid esters can be prepared industrially by carbonylation of olefins, for example by reaction of ethylene, propylene or butylene with carbon monoxide and alkanols in the presence of carbonyl complexes of metals of group VIII of the periodic table. If diolefins, eg. 1,3-butadiene, are used as starting materials, adipic acid esters, which are valuable starting materials for fiber raw materials, are obtained via the intermediate pentenoic acid esters. Since carbon monoxide frequently contains small amounts of hydrogen or hydrogen may be formed during the reaction by conversion of entrained water, the carbonylation reaction is accompanied by a hydroformylation reaction. This leads to aldehydes which, by reaction with the alcohols present, give acetals. If the boiling points of the acetals and aldehydes are very close to those of the esters produced, removal of the undesired aldehydes and acetals by distillation is extremely expensive in industrial operation. On the other hand, the removal of aldehydes and acetals is particularly important in the case of the preparation of adipic acid esters, since the adipic acid prepared from the esters otherwise contains monocarboxylic acids and is hence of a quality which is rather undesirable for the preparation of polymers. Furthermore, even small amounts of aldehydes and acetals lead to undesirable discolorations of the products obtained.

It is an object of the present invention to provide a process whereby acetals and/or aldehydes can be removed in a simple manner from carboxylic acid esters.

We have found that this object is achieved by a process for the purification of carboxylic acid esters which contain aldehydes and/or acetals and which have been obtained by carbonylation of olefinically unsaturated compounds with carbon monoxide and alkanols, wherein the said esters are treated with strongly acidic agents, with or without addition of water.

The novel process has the advantage that the esters are freed in a simple manner from aldehyde or acetal contaminants, which according to the prior art can only be removed at considerable expense by means of multistage purification processes. The carboxylic acid esters purified by the novel process are very pure, since the acetals and aldehydes are removed quantitatively.

The invention is based on the general inventive concept of converting the acetals, which have boiling points close to the carboxylic acid esters, into vinyl ethers by means of acidic agents and removing the ethers as volatiles, or converting the acetals and aldehydes into high-boilers by aldolization and remove them in this form. Accordingly, the process is also applicable to hydrocarbons, ethers, ketones, halogen compounds and aromatic hydrocarbons which are contaminated with acetals and/or aldehydes.

Preferred carboxylic acid esters are obtained by carbonylation of $C_1$–$C_{12}$-monoolefins, $C_4$–$C_{12}$-diolefins, $C_5$–$C_{12}$-cycloalkenes or $C_1$–$C_8$-alkyl esters of $C_3$–$C_{12}$-alkenemonocarboxylic acids. The carbonylation is effected in accordance with conventional methods by reaction with carbon monoxide and $C_1$–$C_8$-alkanols, especially $C_1$–$C_4$-alkanols, for example at from 100° to 200° C. and under pressures of from 50 to 1,000 bar, in the presence of carbonyl complexes of metals of group VIII of the periodic table, especially in the presence of cobalt carbonyl complexes or rhodium carbonyl complexes. The reaction gives $C_3$–$C_{13}$-monocarboxylic acid esters of alkanols of 1 to 8 carbon atoms, $C_6$–$C_{14}$-dicarboxylic acid esters of alkanols of 1 to 8 carbon atoms or cycloalkanecarboxylic acid esters of 5 to 12 carbon atoms in the ring. Saturated monocarboxylic acid esters and dicarboxylic acid esters having the above number of carbon atoms are particularly preferred. Esters prepared in this way contain aldehydes and/or acetals as by-products, the aldehyde part of the acetal having the same number of carbon atoms as the carboxylic acids from which the esters are derived. In addition, the acetals contain the radicals which correspond to the alkanols also used in the reaction. The content of aldehydes and/or acetals is, for example, from 0.1 to 15% by weight. Suitable processes of carbonylation are described, for example, in U.S. Pat. No. 3,176,028 and German Laid-Open Application DOS 1,618,156.

$C_1$–$C_4$-Alkyl adipates which have been obtained by carbonylation of butadiene or of $C_1$–$C_4$-alkyl pentenoates with carbon monoxide in the presence of $C_1$–$C_4$-alkanols are of particular industrial importance. A typical mixture for example contains, in addition to the adipic acid ester, 9–14% by weight of methylglutaric acid ester, 2–5% by weight of ethylsuccinic acid ester, 0.1–0.3% by weight of 5-formylvaleric acid ester and 0.2–0.5% by weight of 6,6-dimethoxycaproic acid ester. Suitable processes for the preparation of alkyl adipates by carbonylation are described, for example, in U.S. Pat. No. 2,801,263 and German Pat. No. 2,713,195.

Preferred strongly acidic agents are sulfuric acid, phosphoric acid, benzenesulfonic acid, toluenesulfonic acid and strongly acidic ion exchangers (crosslinked polystyrene bearing sulfonic acid groups). The lastmentioned, and sulfuric acid, and particularly preferred. Though the strongly acidic agents can be used in merely catalytic amounts, it is advantageous to use them in amounts of from 1 to 50% by weight, based on the content of aldehydes and/or acetals. However, the amount employed is not critical. The treatment is advantageously carried out at from 20° to 200° C., more particularly at from 80° to 140° C.

In purifying carboxylic acid esters which contain only acetals as impurities, it is advantageous to cleave the acetals, by treatment with the above acidic agents at the above temperatures, into vinyl ethers and alkanols. Since this is an equilibrium reaction, it is advantageous to remove the alkanol liberated, for example by stripping with an inert gas, such as nitrogen. Advantageously, the treatment is carried out in the absence of water, in order to avoid possible hydrolysis of the vinyl ether to aldehyde and alkanol. After the treatment, the vinyl ether is removed by distillation.

Carboxylic acid esters which contain only aldehydes, or both aldehydes and acetals as impurities, are industrially particularly important. In such cases, these impurities are advantageously converted into high-boilers. First, the acetals are cleaved, by means of the above acidic agents, to give vinyl ethers and alkanols, and here again the alkanols are advantageously removed, for example by stripping with an inert gas. By operating in the presence of water, advantageously of from 0.5 to 5 moles, especially from 0.8 to 2 moles, of water per mole of acetal, the vinyl ethers are hydrolyzed to aldehydes and alkanols. Higher water contents than those stated, for exampe up to 10 moles per mole of acetal, may also be used without disadvantage. At the temperatures stated, the aldehydes form aldols, thus giving high-boilers which can easily be separated off. The treatment can be carried out batchwise but is advantageously carried out continuously, the acetals being cleaved in a first stage, at the stated temperatures, with the above strongly acidic agents and in the presence of the stated amounts of water, and the alkanols being removed, whilst in a second stage the aldehydes are aldolized, at the stated temperatures, to give high-boilers.

The esters which have been purified in accordance with the invention may be used as solvents. Adipic acid esters purified in this way may be hydrolyzed to adipic acid, which is a starting material for the preparation of polycondensates, eg. nylon 6,6.

The Examples which follow illustrate the process according to the invention.

EXAMPLE 1

1,000 g of dimethyl adipate containing 0.75% of methyl 6,6-dimethoxycaproate, are stirred with 20 g of anhydrous phosphoric acid at 110° C. in a 2 liter round-bottomed flask equipped with a reflux condenser and gas inlet, and the methanol liberated is stripped with 50 liters/h of nitrogen. After 2.5 hours the mixture is cooled, the phosphoric acid is then separated off and finally the organic product is subjected to fractional distillation at 20 mbar. 983 g of pure dimethyl adipate are obtained; according to analysis by gas chromatography, this product no longer contains any methyl 6,6-dimethoxycaproate.

EXAMPLE 2

2 liters per hour of dimethyl adipate are fed into a cascade consisting of a heated 10 liter stirred kettle which is equipped with a condenser and gas inlet and contains 2.5 liters of a macroporous acidic ion exchanger, and a downstream 1.8 meter long flow tube (internal diameter 6 cm) which is filled with the same ion exchanger and through which the material flows downward. The dimethyl adipate is contaminated with 0.3% of methyl 6,6-dimethoxycaproate and 0.25% of methyl 5-formylvalerate and has a water content of 0.1%. The stirred kettle and flow tube are heated to 120° C.; the methanol liberated in the stirred kettle is stripped off with 100 liters/h of pure nitrogen. The mixture of dimethyl adipate and high-boilers discharged from the bottom of the flow tube is fed to a distillation under reduced pressure. The dimethyl adipate obtained from this distillation is completely free from methyl 6,6-dimethoxycaproate and methyl 5-formylvalerate and is 99.9% pure.

We claim:

1. A process for purifying carboxylic acid esters which have been obtained by carbonylizing olefinically unsaturated compounds with carbon monoxide and alkanols and which contain color formers including aldehydes or acetals, wherein the said esters are contacted with strongly acidic agents of preselected kind and concentration sufficient to reduce said color formers sufficiently to provide a polymer grade ester product, with or without addition of water.

2. The process of claim 1, wherein sulfuric acid, phosphoric acid, benzenesulfonic acid, toluenesulfonic acid or a strongly acidic ion exchanger is used.

3. The process of claim 1, wherein from 1 to 50% by weight, based on the content of aldehydes and/or acetals, of the strongly acidic agent is used.

4. The process of claim 1, wherein the treatment is carried out at from 80° to 140° C.

5. The process of claim 1, wherein the carboxylic acid esters containing acetals are treated in the absence of water, with removal of the alkanol split off, and the resulting vinyl ether is removed by distillation.

6. The process of claim 1, wherein carboxylic acid esters which contain aldehydes, or aldehydes and acetals, are treated in the presence of water, with removal of the alkanol split off, and the carboxylic acid esters are separated by distillation from the high-boilers formed.

7. The process of claim 1, wherein dimethyl adipate which is contaminated with methyl 5-formylvalerate and/or methyl 6,6-dimethoxycaproate is used as the starting mixture.

* * * * *